United States Patent [19]

Lazarus et al.

[11] Patent Number: 4,792,330
[45] Date of Patent: Dec. 20, 1988

[54] COMBINATION CATHETER AND DUCT CLAMP APPARATUS AND METHOD

[75] Inventors: Harrison M. Lazarus, Salt Lake City; Dixon A. Ford, Farmington, both of Utah

[73] Assignee: Lazarus Medical Innovations, Inc., Salt Lake City, Utah

[21] Appl. No.: 72,796

[22] Filed: Jul. 13, 1987

[51] Int. Cl.$^4$ ............................................. A61B 17/00
[52] U.S. Cl. .................................. 604/174; 128/346; 128/DIG. 26
[58] Field of Search .................... 128/303 R, 319, 321, 128/322, 325, 326, 346, DIG. 12, DIG. 26; 604/174

[56] References Cited

U.S. PATENT DOCUMENTS

| | | |
|---|---|---|
| D. 275,790 | 10/1984 | Marlowe ............................. 128/322 |
| 292,846 | 2/1884 | Nye et al. . |
| 319,775 | 6/1885 | Barney . |
| 1,555,823 | 10/1925 | Bernard . |
| 2,602,357 | 7/1952 | Nash . |
| 2,642,871 | 6/1953 | Thuerig . |
| 2,952,175 | 9/1960 | Edlen et al. . |
| 3,126,005 | 3/1964 | Smialowski . |
| 3,166,819 | 1/1965 | Robbins ............................. 128/325 |
| 3,613,683 | 10/1971 | Kees, Jr. . |
| 3,786,816 | 1/1974 | Wolvek . |
| 3,814,080 | 6/1974 | Norman . |
| 3,828,791 | 8/1974 | Santos ............................... 128/321 |
| 3,840,018 | 10/1974 | Heifetz . |
| 3,926,195 | 12/1975 | Bleier . |
| 3,952,619 | 4/1976 | Cook . |
| 4,106,508 | 8/1978 | Berlin . |
| 4,165,746 | 8/1979 | Burgin .............................. 128/321 |
| 4,192,313 | 3/1980 | Ogami . |
| 4,453,536 | 6/1984 | Abild .............................. 128/346 |
| 4,462,404 | 7/1984 | Schwartz . |
| 4,484,911 | 11/1984 | Berlin et al. . |
| 4,487,204 | 12/1984 | Hrouda . |

OTHER PUBLICATIONS

Padula et al., "A New Clamp for Rapid Vascular Anastomosis," *Surgery*, vol. 57, #6, 6/1975, pp. 819-822.
Skillings, John C. et al., "Cost-Effectiveness of Operative Cholangiography," *The American Journal of Surgery*, pp. 26-31 (vol. 137, 1979).
Taufic, Mansur, "A Safe and Secure Technique of Cystic Duct Catherterization," *Archives of Surgery*, vol. 114, pp. 749-751 (Jun. 1979).
Pagana, Timothy J., et al., "Indications and Accuracy of Operative Cholangiography," *Archives of Surgery*, vol. 115, pp. 1214-1215 (Oct. 1980).
Kitahama, Akio, et al., "Routine Intraoperative Cholangiogram," *Surgery, Gynecology & Obstetrics*, vol. 162, pp. 317-322 (1986).
"Intraoperative Cholangiography: Now Obligatory?," *Surgical Capsule & Comment*, p. 11 (Fall 1986).
Hampson, L.G., et al., "A Simple Method for Catheter Fixation of the Cystic Duct Cholangiography," *Surgery, Gynecology & Obstetrics*, vol. 159, p. 83, 1984.
Berci, George, et al., "Improved Cannula for Operative (Cystic Duct) Cholangiography," *The American Journal of Surgery*, vol. 137, pp. 826-828, Jun. 1979.

*Primary Examiner*—Stephen C. Pellegrino
*Assistant Examiner*—Ralph Lewis
*Attorney, Agent, or Firm*—Workman, Nydegger & Jensen

[57] ABSTRACT

A combination catheter and duct clamp apparatus and method. The apparatus includes a hollow member with a substantially planar clamping surface at one end and a sliding member with a substantially planar clamping surface at one end which is telescopically slidable within the hollow member. A spring maintains an essentially constant clamping pressure between the clamping surfaces.

The clamp is ideally suited for use during cholangiography where it may be used for inserting a catheter within the cystic duct and for thereafter clamping the cystic duct around the catheter. The clamping pressure provides an adequate seal of the cystic duct and does not occlude the inserted catheter. Multiple clamping angles give the clamp unique versatility during the surgical procedure. Being constructed out of a radiolucent material, the clamp may be left in place while a cholangiogram is taken without interfering with the completed cholangiogram.

37 Claims, 4 Drawing Sheets

COMBINATION CATHETER AND DUCT CLAMP APPARATUS AND METHOD

BACKGROUND

1. The Field of the Invention

The invention relates to surgical clamps, and more particularly to surgical clamps which perform dual clamping functions. The present invention is designed for securely clamping a catheter for insertion within an anatomical duct and for thereafter clamping the duct around the catheter with an essentially constant clamping pressure so that the duct is adequately sealed without occluding the inserted catheter.

2. The Prior Art

Surgical clamps perform a vital function during any operative procedure. Surgical clamps function as an extension of the surgeon's hands, enabling the surgeon to hold and manipulate anatomical parts or other surgical instruments. Surgical clamps are often developed to make some step in a surgical procedure easier for the surgeon.

For example, operative cholangiography, since its introduction in 1932, has witnessed the development of various clamps and other devices to make the procedure faster, easier, and more reliable.

In performing operative cholangiography, the cystic duct is cleaned off near the gallbladder and is occluded with a tie or clamp depending on the surgeon's discretion. The cystic duct is then incised, creating an opening so that a catheter can be inserted within the duct. Next, the cystic duct catheter is grasped with a clamp and inserted into the opening of the cystic duct. After the catheter is inserted into the desired position (the catheter is to be in the common duct, but not so far that it is into the duodenum), the catheter is securely held in place by either a hemoclip or ligature. A radiopaque dye is thereafter injected through the cystic duct catheter and x-rays are taken (known as cholangiograms).

Operative cholangiography is basically an x-ray examination of the bile ducts to determine whether gallstones exist. The procedure is performed routinely during a cholecystectomy (removal of gallbladder) which is the second most common intraabdominal operation performed in the United States. If, after examining the cholangiogram, gallstones are observed in the bile ducts, they are removed before the cholecystectomy is completed.

In recent years, there has been considerable interest in developing improved methods of performing cholangiographies as well as improved surgical instruments for use in a cholangiography. Much of the attention has focused on the method of holding the catheter in position within the cystic duct.

For example, after the catheter has been inserted into the cystic duct it has been traditionally held in place with a ligature. Ligatures, however, are very inconvenient for the surgeon. They take time, and time is always a factor during any surgical procedure, particularly when the patient is under anesthetic. Furthermore, ligatures may damage the cystic duct.

Alternatively, surgeons have used hemoclips to hold the catheter in place after it has been inserted into the cystic duct. Hemoclips, which are designed specifically for occluding blood vessels, are fast and easy to use. However, it is very difficult to control how much pressure is placed on the hemoclip. As a result, the surgeon often inadvertently crushes the catheter when a hemoclip is applied. Only with much practice may hemoclips be applied without occluding the catheter or damaging the cystic duct. This is because most hemoclips are applied with a specially designed clamp which typically releases the hemoclip only after it has been fully clamped.

If the catheter is occluded, then the diagnostic dye cannot be injected into the common bile duct and a cholangiogram cannot be taken. In addition, once a hemoclip is in place it is difficult for the surgeon to release the hemoclip and remove the catheter from the cystic duct. Thus, although hemoclips have been advocated by some (see, e.g., Hampson, et al., "A Simple Method for Catheter Fixation of the Cystic Duct During Cholangiography," 159 *Surgery, Gynecology, and Obstetrics* 82–83 (1984), the use of hemoclips has several significant drawbacks.

One problem which has faced those skilled in the art is how to hold the catheter in place after it has been inserted within the cystic duct so that the catheter is not crushed and so that the diagnostic dye does not leak into the surrounding wound. An additional problem which has faced those skilled in the art is the necessity of using multiple clamps during cholangiography. For instance, one clamp is usually required to grasp and insert the catheter within the cystic duct and another clamp is used to hold the catheter within the cystic duct while a ligature or hemoclip is applied. Because the abdominal wound during cholangiography is so small and deep, multiple clamps are inconvenient.

Although various attempts to solve these problems have been made by those skilled in the art, to date there has not been devised an apparatus and method that have fully succeeded in achieving a solution to these problems.

One prior art approach to solve these problems has been the use of a single modified cystic duct clamp with two holes of different diameters drilled into its curved end. The smaller hole is designed for holding the catheter alone and the larger hole is designed for holding the catheter within the cystic duct while a ligature is applied. See, e.g., Taufic, "A Safe and Secure Technique of Cystic Duct Catheterization," 114 *Archives of Surgery* 749–51 (June 1979).

This technique has several significant drawbacks. Chief among them is that even though a single clamp instead of two is used, a ligature is still necessary to hold the catheter in place within the cystic duct. The clamp may not be used while the cholangiogram is taken because the clamp is made out of a radiopaque material which tends to interfere with the quality of the cholangiogram. Additionally, because the modified cystic duct clamp is of a traditional scissors-clamp configuration, the clamp takes up too much space within the small, deep wound.

Another prior art approach has been to use metal catheters instead of plastic catheters. This technique eliminates the risk of having the catheter crushed after a hemoclip is applied. Furthermore, metal catheters may be inserted within the cystic duct manually, thereby eliminating the need for a separate clamp to be used in inserting the catheter. See, e.g., Berci et al., "Improved Cannula for Operative (Cystic Duct) Cholangiography," 137 *The American Journal of Surgery* 826–28 (June 1979).

Despite its advantages, this technique is not preferred simply because a metal catheter is radiopaque and would therefore tend to interfere with the cholangiogram. Furthermore, a metal catheter with a fixed shape may easily perforate the cystic duct or common duct.

Yet another prior art approach to these problems has been to use a modified Borge clamp to hold the catheter in place within the cystic duct instead of a hemoclip or ligature. See, e.g., Berci et al., supra. The round hole of a normal clamp was milled square thereby giving the clamp a larger range of closure. Such a modified clamp holds the catheter tightly within the cystic duct but without occluding the catheter. In addition, it is easier to release the catheter in the cystic duct held with a clamp than to remove a hemoclip.

Although this technique has advantages compared to using a hemoclip to hold the catheter within the cystic duct, several disadvantages have been observed. Because the clamp is constructed out of a radiopaque material, the clamp tends to interfere with the desired cholangiogram. It is, therefore, possible that certain gallstones or other abnormalities might go undetected if such a clamp is used.

More importantly, the modified Borge clamp is a squeeze locking or ratchet clamp. The clamping pressure exerted at the "jaws" of the clamp is directly related to the quantity of material between the jaws. Thus, two identical clamps at the same ratchet position could be exerting vastly different clamping pressures depending on the material between the jaws. Therefore, there is a serious risk of damage to the duct or catheter when such clamps are used.

Still another approach that has been tried is to use a balloon catheter which will permit the diagnostic dye to be injected into the bile ducts and at the same time occlude the cystic duct so that no dye leaks into the surgical wound. Balloon catheters are inadequate for use in cholangiography because even a slight overinflation of the balloon could easily rupture the cystic duct.

In summary, none of the prior art techniques and apparatus developed to date provide adequate solutions to the problem of properly holding a catheter in place within the cystic duct, while eliminating the problems inherent in providing adequate securement of the catheter without occluding the x-rays, and without undue complication.

From the foregoing, it will be appreciated that what is needed in the art are apparatus and methods for clamping an anatomical duct into which a catheter has been inserted with an essentially constant clamping pressure which is not so great that the catheter is crushed nor too little that diagnostic dye is leaked into the abdominal wound.

Additionally, it would be a significant advancement in the art to provide apparatus and methods which perform the dual function of clamping a catheter prior to insertion within an anatomical duct and for thereafter securely clamping the duct around the catheter, so that only a single instrument need be used.

It would be another advancement in the art to provide an apparatus and method for a surgical clamp which readily accommodates use thereof in deep wounds or other congested operating sites.

It would be a further advancement in the art to provide an apparatus and method for use of a surgical clamp which is constructed out of a radiolucent material in the area of the duct so that the surgical clamp may be used while an x-ray is taken and will not interfere with the completed x-ray.

It would be yet another advancement in the art to provide an apparatus and method for use of a surgical clamp which can clamp an anatomical duct without damaging the duct.

The foregoing, and other features and objects of the present invention, are realized in the combination catheter and duct clamp which are disclosed and claimed herein.

BRIEF SUMMARY AND OBJECTS OF THE INVENTION

The present invention is directed to a surgical clamp and its method of use during cholangiography. The clamp includes a novel telescopic clamping arrangement and a spring which provides an essentially constant clamping pressure. The clamp is designed to provide just enough clamping pressure to securely hold a catheter within the cystic duct and prevent any leakage of the diagnostic dye yet not too much clamping pressure which would crush or occlude the catheter within the cystic duct. The present invention also includes two different clamping angles which provide the surgeon unique versatility in using the clamp. The clamp also is constructed of a radiolucent material in the area of the clamping surfaces so that the clamp may be left in place while a cholangiogram is taken without interfering with the completed cholangiogram.

It is, therefore, an object of the present invention to provide a surgical clamp which is self clamping at an essentially constant clamping pressure.

Another important object of the present invention is to provide a surgical clamp and method for use which perform the dual purpose of securely holding a catheter for insertion within the cystic duct and for thereafter clamping the cystic duct around the catheter.

An additional important object of the present invention is to provide a surgical clamp and method for use which will clamp the cystic duct around a catheter with sufficient clamping pressure to prevent diagnostic dye from leaking into the abdominal wound and yet not occlude the catheter within the duct.

Still another object of the present invention is to provide a surgical clamp which is constructed out of a radiolucent material and does not interfere with a cholangiogram taken during the cholangiography.

A further important object of the present invention is to provide a surgical clamp and method for use which may be used in deep wounds or other congested operating sites without interfering with other surgical instruments placed within the wound.

Yet another object of the present invention is to provide a surgical clamp and method which will safely clamp an anatomical duct without damaging the duct.

These and other objects and features of the present invention will become more fully apparent from the following description and appended claims taken in conjunction with the accompanying drawings.

DETAILED DESCRIPTION OF THE PREFERRED EMBODIMENTS

Figure 1:
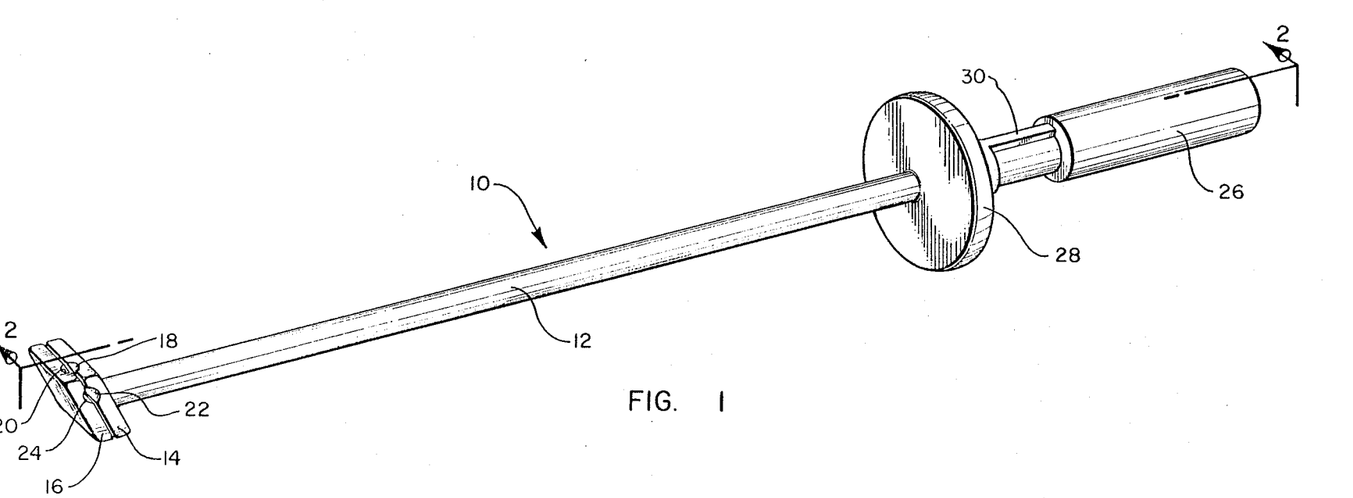
FIG. 1 is perspective view of one presently preferred embodiment of the present invention.
Figure 2:
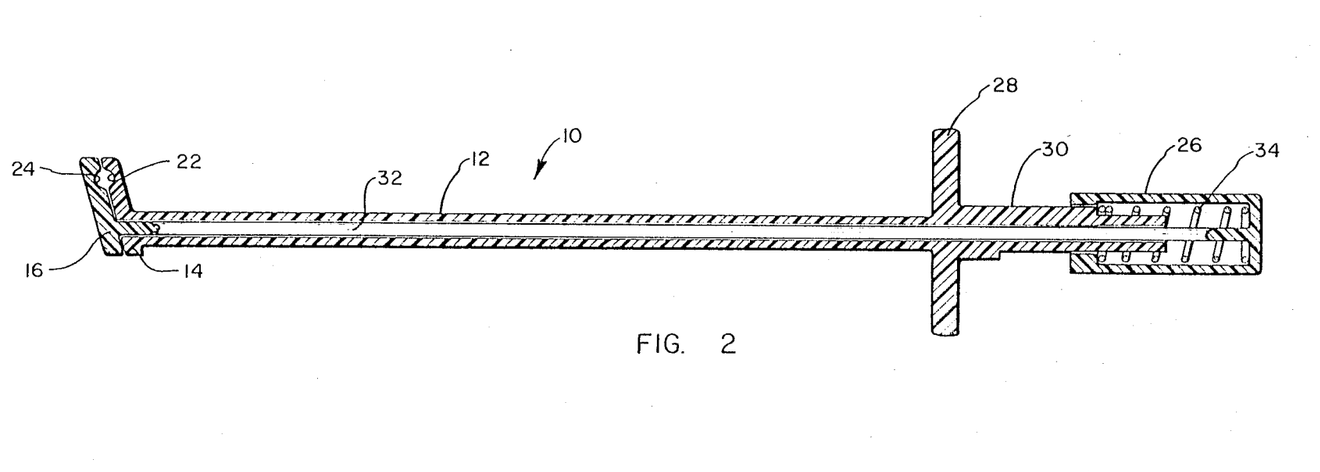
FIG. 2 is a cross-sectional view of FIG. 1 taken along line 2—2 of FIG. 1.

Reference is now made to the drawings wherein like parts are designated with like numerals throughout. Referring first to FIGS. 1 and 2, one presently preferred embodiment of the apparatus of the present invention is illustrated and generally designated 10.

Surgical clamp 10 is particularly designed for use during cholangiography. The apparatus includes a hollow member 12 having at one end a substantially planar clamping surface 14 and at the other end finger wings 28. A sliding member 32 having at one end a substantially planar clamping surface 16 and at the other end a push knob 26 is located within the hollow member 12 so as to be telescopically slidable therethrough.

A spring 34 is located between the finger wings 28 of the hollow member 12 and the push knob 26. The spring 34 serves to maintain an essentially constant clamping pressure between the two clamping surfaces 14 and 16.

Clamping surface 14 contains two orthogonal grooves 18 and 22. Clamping surface 16 also contains two orthogonal grooves 20 and 24 which match orthogonal grooves 18 and 22 of clamping surface 14. Grooves 18, 20, 22, and 24 serve to enhance the surgeon's ability to grasp a catheter during insertion into the cystic duct and also permit the cystic duct to be clamped around the catheter without crushing the catheter.

These orthogonal grooves and the hollow member 12 define two different clamping angles. For example, orthogonal grooves 22 and 24 correspond to a clamping angle of approximately 90°. Similarly, orthogonal grooves 18 and 20 correspond to a clamping angle of approximately 105° to 110°. These two clamping angles give the surgeon greater flexibility in using the surgical clamp. It will be appreciated that the surgical clamp design may be altered to accommodate other clamping angles depending on the surgical procedure for which the clamp is used.

The hollow member 12 further contains a ridge 30 which interacts with the push knob 26 and serves to prevent the sliding member 32 from rotating within the hollow member 12, thus maintaining grooves 18, 20, 22, and 24 in respective alignment of one another. Ridge 30, therefore, prevents clamping surfaces 14 and 16 from pivoting relative to each other.

Other means may also be used to prevent clamping surfaces 14 and 16 from pivoting relative to each other. For instance, hollow member 12 may have an inside cross-sectional square configuration and sliding member 32 may also have a square cross-section. Thus, sliding member 32 may still telescopically extend from hollow member 12, but due to its square cross-section, sliding member 12 will not rotate within hollow member 12. It will be appreciated other cross-sectional geometric configurations may be used which accomplish the purpose of preventing the sliding member 32 from rotating within the hollow member 12.

The sliding member 32 and hollow member 12 are preferably constructed out of a radiolucent material. Hence, the surgical clamp may then be used to hold a catheter in place within the cystic duct while diagnostic dye is injected through the catheter into the cystic duct and while a cholangiogram is taken without any risk of interfering with the completed cholangiogram.

Figure 4:
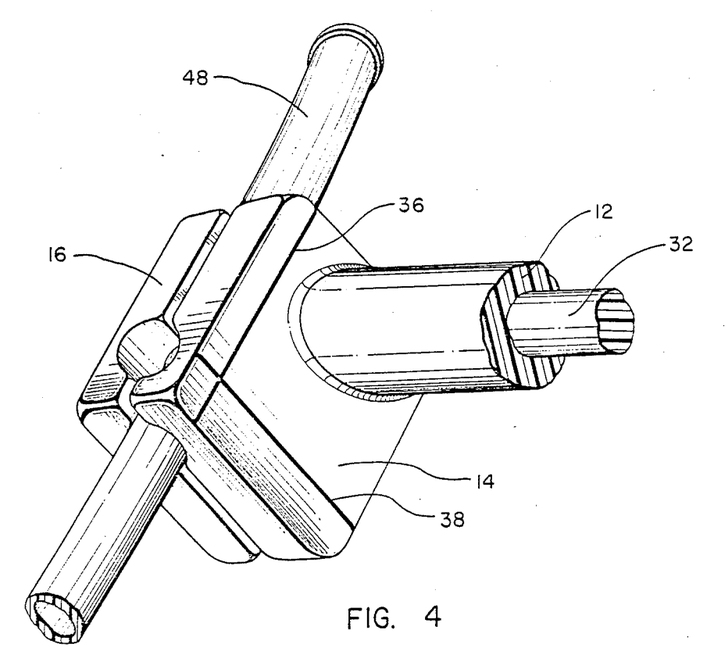
FIG. 4 is a close-up perspective view of the surgical clamp holding the catheter in place taken around line 4—4 of FIG. 3.
Figure 7:
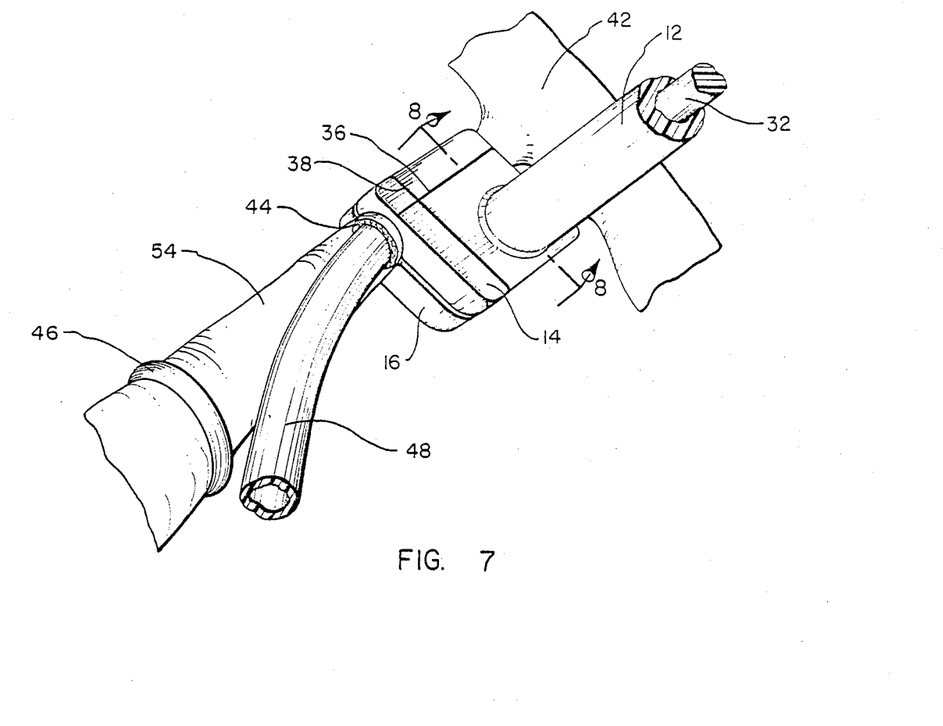
FIG. 7 is a perspective view of the surgical clamp in the process of clamping the cystic duct around a catheter which was inserted within the cystic duct.

Clamping surface 14 contains two position indicator lines 36 and 38 as illustrated in FIGS. 4 and 7. Indicator lines 36 and 38 visibly correspond to orthogonal grooves 22 and 18, respectively. The surgeon can, therefore, be sure the catheter or cystic duct is properly clamped by lining the catheter or duct up with indicator lines 36 or 38.

Indicator lines 36 and 38 may also be constructed out of a fine radiopaque material such as a metal filament. Therefore, the indicator lines will mark the location of the surgical clamp on the completed cholangiogram without obscuring important features of the cholangiogram. It will be appreciated that indicator lines 36 and 38 may alternatively be attached to clamping surface 16 rather than clamping surface 14.

The surgical clamp functions by placing two fingers on the finger wings 28 and depressing the push knob 26 with the thumb. The sliding member 32 telescopically extends from hollow member 12. In this manner, the clamping surfaces 14 and 16 may be opened. The spring 34 provides an essentially constant clamping pressure so that when the thumb releases the push knob 26, clamping surfaces 14 and 16 automatically clamp together. Thus, spring 34 and push knob 26 serve to releasably bias sliding member 32 at a desired clamping position.

The method of using the surgical clamp during cholangiography can be best understood with reference to FIGS. 3 to 8.

Cholangiography is typically an intraoperative procedure performed during a cholecystectomy. The purpose of the cholangiography is to obtain an x-ray examination of the bile ducts to determine if there are any hidden gallstones which need to be removed or other abnormality which needs to be corrected.

The operation proceeds by having the abdomen open with the gall bladder and ductal structures freed up. These ductal structures are well below the surface of the abdomen (approximately 6 to 20 centimeters). Therefore, surgical instruments of some length must be used to reach the cystic duct. The cystic duct 54, which extends from the gallbladder 40, unites with the hepatic ducts 50 and 52 from the liver to form the common bile duct 42. The pancreatic duct also joins the common bile duct before it empties into the duodenum.

Figure 3:
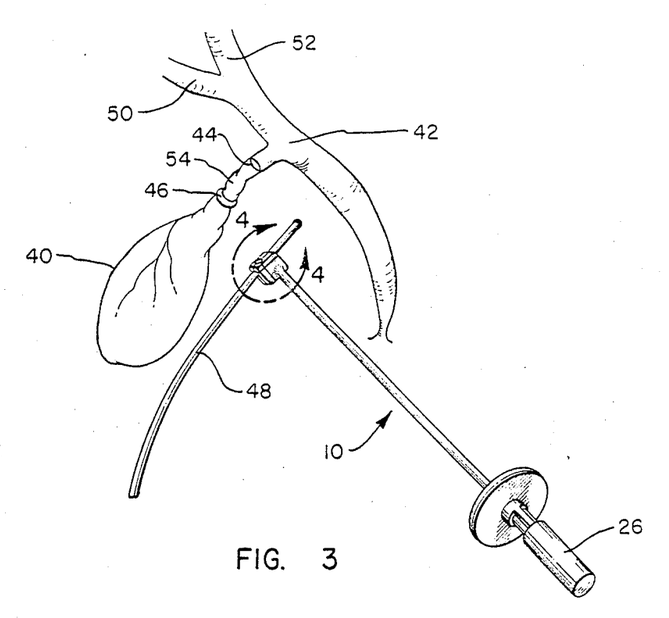
FIG. 3 is a perspective view illustrating the surgical clamp holding a catheter prior to insertion within an incision in the cystic duct.

The cystic duct 54 is cleaned off near the gallbladder 40 and is occluded with a tie or clamp 46 depending on the surgeon's discretion. Next, the cystic duct is incised creating an opening 44 so that the catheter 48 can be inserted. Upon incising the cystic duct, bile is readily visualized. The cystic duct catheter 48 is then grasped by the surgical clamp 10 at a distance of approximately 1 to 5 centimeters from the tip of the catheter as illustrated in FIG. 3. The surgical clamp securely holds the catheter so it can be directed into the opening 44 in the cystic duct 54. The clamp is long enough so it can reach the opening.

Once the catheter 48 clearly enters the cystic duct 54, the surgical clamp 10 is then moved more distally on the catheter. This is accomplished by simply depressing the push knob 26, sliding the clamp further up the catheter from the inserted end, and then regripping the catheter by releasing the push knob 26. The catheter can then be advanced further into the cystic duct. The desired length (approximately 5 to 10 centimeters) of the catheter 48 is inserted into the cystic duct 54 so that the catheter is clearly into the common duct 42 but not so far that it is into the duodenum.

Figure 8:
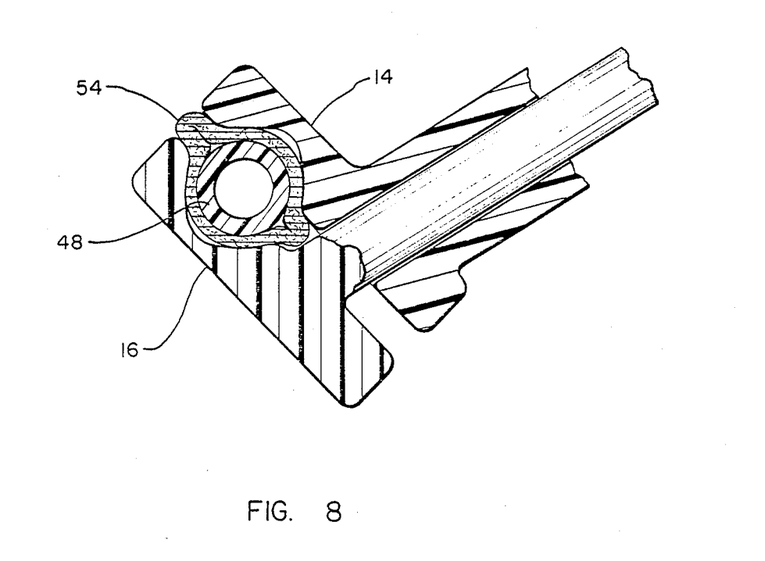
FIG. 8 is a cross-sectional view of FIG. 7 taken along line 8—8 of FIG. 7, illustrating how the catheter is securely held within the cystic duct without crushing the catheter.

Once the catheter is properly inserted within the cystic duct, the push knob is then depressed to release the catheter. The clamp is then moved to a position along the cystic duct where the catheter has been inserted and the push knob is released thereby permitting the surgical clamp to clamp the cystic duct around the catheter as illustrated in FIGS. 7 and 8. The surgical clamp will securely hold the catheter 48 within the cystic duct 54 in the desired position without crushing or occluding the catheter. A diagnostic dye can then be injected into the catheter as desired. After satisfactory cholangiograms are obtained, the push knob is simply depressed to free the catheter which is then removed and the operation proceeds in a normal manner.

Figure 5:
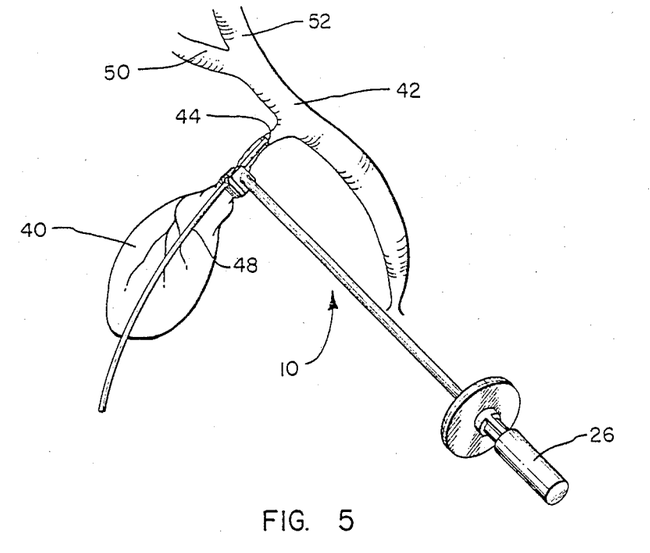
FIG. 5 is a perspective view of the surgical clamp holding a catheter while the catheter is inserted within the cystic duct illustrating the use of one of the clamping angles of the surgical clamp.
Figure 6:
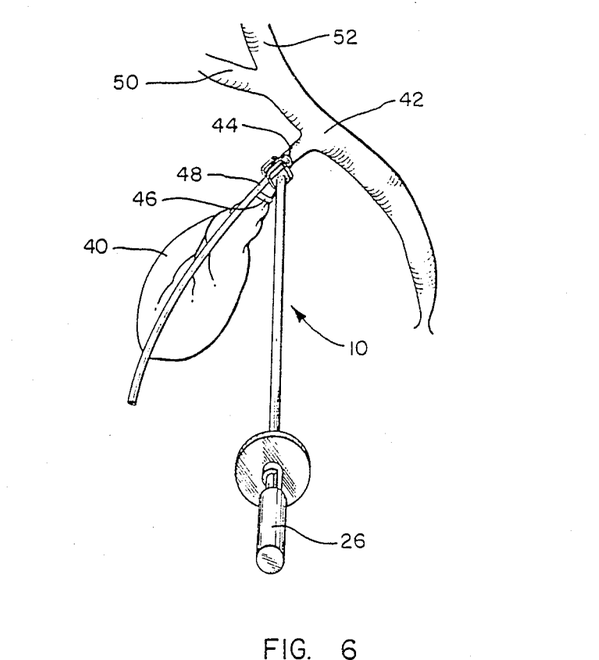
FIG. 6 is a perspective view of the surgical clamp holding a catheter while the catheter is inserted within the cystic duct similar to FIG. 5, yet illustrating the use of a another clamping angle of the surgical clamp.

FIGS. 5 and 6 illustrate the unique versatility the surgical clamp possesses due to its two distinct clamping angles. Depending on the patient, different clamping angles are needed for the surgeon to manipulate and insert the catheter within the cystic duct or to clamp the cystic duct around the catheter. Multiple clamping angles on one surgical clamp, therefore, eliminates the need for multiple clamps.

FIGS. 7 and 8 illustrate how the surgical clamp may be used to hold the catheter in place after it has been inserted within the cystic duct. In particular, FIG. 8 shows how the cystic duct forms a tight seal around the catheter. In this way, after diagnostic dye is injected through the catheter, the dye will not leak backwards out of the cystic duct into the surgical wound. FIG. 8 also illustrates how the surgical clamp does not crush or occlude the catheter when it is being held in place within the cystic duct.

Although the present discussion relates to a surgical clamp for use during cholangiography, it will be appreciated that the apparatus and methods discussed may be readily adapted for use with other similar surgical procedures. Examples of commonly performed surgical procedures for which the present invention may be used include arteriography, venography, ureterography, and pancreatography. The present invention may also be used during other surgical procedures where a catheter or other surgical instrument is inserted and clamped within a ductal or tubular structure.

From the foregoing, it will be appreciated that the present invention provides a combination catheter and duct clamp apparatus and method for clamping a catheter or a duct, into which the catheter has been placed, with an essentially constant clamping pressure which is not too great so that the catheter is crushed within the clamp nor too little so that diagnostic dye is leaked into the abdominal wound.

Additionally, it will be appreciated that the present invention further provides a combination catheter and duct clamp apparatus and method which perform the dual function of clamping a catheter for insertion within an anatomical duct and for thereafter clamping the duct around the catheter.

Likewise, it will be appreciated that the present invention also provides a combination catheter and duct clamp apparatus and method for use in deep wounds or other congested operating sites.

It will also be appreciated that the present invention provides a combination catheter and duct clamp apparatus and method for use of a surgical clamp during cholangiography which is constructed out of radiolucent material so that the surgical clamp may be used while an x-ray is taken and will not interfere with the completed x-ray.

Finally, it will be appreciated that the present invention provides a combination catheter and duct clamp apparatus and method for clamping an anatomical duct which substantially reduces the risk of damage to the duct.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A surgical apparatus for inserting a catheter into an anatomical duct and for thereafter clamping the duct around the catheter, said apparatus comprising:
   a stationary member comprising at a distal end thereof a first clamping member having a first clamping surface;
   a sliding member comprising at a distal end thereof a second clamping member having a second clamping surface, said sliding member being longitudinally slidable relative to said stationary member to accomodate selective movement of said second clamping surface from a first clamping position to a second clamping position, said first and second clamping surfaces each comprising a groove such that the grooves of said clamping surfaces cooperatively define an opening therebetween for receiving said catheter such that the apparatus does not occlude said catheter when held in said opening; and
   means for releasably biasing said sliding member at said first clamping position, and for releasing said sliding member to accommodate movement of said sliding member to said second clamping position, such that said catheter may be clamped by said apparatus when in said first clamping position so as to secure said catheter for insertion into said duct, and such that thereafter said catheter may be released and said duct clamped around said catheter when said apparatus is in the second clamping position.

2. A surgical apparatus as defined in claim 1, wherein the stationary member and the sliding member are constructed of a radiolucent material, such that the surgical apparatus may be used while an x-ray is taken without obscuring the resultant x-ray.

3. A surgical apparatus as defined in claim 2, wherein one of said first and second clamping member comprises a radiopaque indicator means such that the surgical apparatus' location on the resultant x-ray may be identified without substantially obscuring the x-ray.

4. A surgical apparatus as defined in claim 1, wherein said first and second clamping members are cooperatively joined to said stationary and sliding members, respectively, so as to define a first clamping angle and a second clamping angle which allow the clamp to function in two different positions rotated from one another about the longitudinal axis of said stationary and sliding members.

5. A surgical apparatus as defined in claim 4, wherein the first clamping angle is approximately 105° to 110° and the second clamping angle is approximately 90°.

6. A surgical apparatus as defined in claim 4, wherein the first and second clamping members each comprise a further groove located on the respective first and second clamping surfaces, said further grooves defining a second opening cooperatively formed between said clamping surfaces, and said second opening being oriented essentially orthogonal to said first opening.

7. A surgical apparatus as defined in claim 6, wherein said first clamping member contains visual indicator means which correspond with said orthogonal grooves on said first clamping surface.

8. A surgical apparatus as defined in claim 1, wherein the stationary member is hollow such that the sliding member is telescopically slidable within the stationary member.

9. A surgical apparatus as defined in claim 1, wherein the first and second clamping members are substantially planar and not coplanar.

10. A surgical apparatus as defined in claim 1, further comprising means for preventing said first clamping member from pivoting relative to said second clamping member.

11. A surgical apparatus as defined in claim 1, wherein the biasing means comprises means for maintaining an essentially constant clamping pressure when said apparatus is in said second clamping position.

12. A surgical clamp for inserting a catheter into an anatomical duct and for thereafter clamping the duct around the catheter, said clamp comprising:
  a hollow member comprising at a distal end thereof a first clamping member having a first clamping surface;
  a sliding member comprising at a distal end thereof a second clamping member having a second clamping surface, said sliding member being telescopically slidable within said hollow member to accommodate selective movement of said second clamping surface relative to said first clamping surface from a first clamping position to a second clamping position, said first and second clamping surfaces each comprising a groove formed thereon such that the grooves of said clamping surfaces cooperatively define an opening therebetween for receiving said catheter such that the clamp does not occlude said catheter when held in said opening; and
  means for releasably biasing said sliding member at said first clamping position, and for releasing said sliding member from said first clamping position and telescopically extending said sliding member to said second clamping position, such that said catheter may be clamped by said clamp when in said first clamping position so as to secure said catheter for insertion into said duct, and such that thereafter said catheter may be released and said duct clamped around said catheter when said clamp is in the second clamping position.

13. A surgical clamp as defined in claim 12, wherein the hollow member and the sliding member are constructed of a radiolucent material, such that the surgical clamp may be used while an x-ray is taken without obscuring the resultant x-ray.

14. A surgical clamp as defined in claim 13, wherein one of said first and second clamping members comprises a radiopaque indicator means such that the surgical clamps location on the resultant x-ray may be identified without substantially obscuring the x-ray.

15. A surgical clamp as defined in claim 12, wherein said first and second clamping members are cooperatively joined to said hollow and sliding members, respectively, so as to define a first clamping angle and a second clamping angle which allow the clamp to function in two different positions rotated from one another about the longitudinal axis of said hollow and sliding members.

16. A surgical clamp as defined in claim 15, wherein the first clamping angle is approximately 105° to 110° and the second clamping angle is approximately 90°.

17. A surgical clamp as defined in claim 15, wherein the first and second clamping members each comprise a further groove located on the respective first and second clamping surfaces, said further grooves defining a second opening cooperatively formed between said clamping surfaces, and said second opening being oriented essentially orthogonal to said first opening.

18. A surgical clamp as defined in claim 17, wherein said first clamping member contains visual indicator means which correspond with said orthogonal grooves on said first clamping surface.

19. A surgical clamp as defined in claim 12, wherein the first and second clamping members are substantially planar and not coplanar.

20. A surgical clamp as defined in claim 12, further comprising means for preventing said first clamping member from pivoting relative to said second clamping member.

21. A surgical clamp as defined in claim 12, wherein the biasing means comprises means for maintaining an essentially constant clamping pressure when said clamp is in said second clamping position.

22. A cholangiographic clamp for inserting a catheter into the cystic duct and for thereafter clamping the duct around the catheter while a cholangiogram is taken, said clamp comprising:
  a hollow member comprising at a distal end thereof a first clamping member having a first clamping surface;
  a sliding member comprising at a distal end thereof a second clamping member having a second clamping surface, said first and second clamping members being cooperatively joined to said hollow and sliding members, respectively, so as to define a first clamping angle and a second clamping angle which allow the clamp to function in two different positions rotated from one another about the longitudinal axis of said hollow and sliding members, said sliding member being telescopically slidable within said hollow member to accommodate selective movement of said second clamping surface relative to said first clamping surface from a first clamping position to a second clamping position; and
  a push knob in communication with said sliding member such that depressing said push knob relative to said hollow member releases said sliding member from said first clamping position and telescopically extends said sliding member to said second clamping position, such that said catheter may be clamped by said clamp when in said first clamping position so as to secure said catheter for insertion into said cystic duct, and such that thereafter said catheter may be released and said cystic duct clamped around said catheter when said clamp is in the second clamping position.

23. A cholangiographic clamp as defined in claim 22, wherein the first and second clamping member are substantially planar and not coplanar.

24. A cholangiographic clamp as defined in claim 23, wherein the first and second clamping members each comprise orthogonal grooves located on the respective first and second clamping surfaces, said orthogonal grooves correspond with said first and second clamping angles.

25. A cholangiographic clamp as defined in claim 24, wherein the hollow member and the sliding member are constructed of a radiolucent material, such that the clamp may be used while an x-ray is taken without obscuring the resultant x-ray.

26. A cholangiographic clamp as defined in claim 25, further comprising means for preventing said sliding member from rotating within said hollow member.

27. A cholangiographic clamp as defined in claim 26, wherein the first clamping angle is approximately 105° to 110° and the second clamping angle is approximately 90°.

28. A cholangiographic clamp as defined in claim 27, wherein one of said first or second clamping members comprises a radiopaque indicator means such that the clamp's location on the resultant x-ray may be identified without substantially obscuring the x-ray.

29. A cholangiographic clamp as defined in claim 24, wherein said first clamping member contains visual indicator means which correspond with said orthogonal grooves on said first clamping surface.

30. A cholangiographic clamp as defined in claim 22, further comprising means cooperative with said hollow member and with said sliding member for maintaining an essentially constant clamping pressure when said clamp is in said second clamping position.

31. A cholangrographic clamp for inserting a catheter into the cystic duct and for thereafter clamping the duct around the catheter while a cholangiogram is taken, said clamp comprising:
  a hollow member comprising at a distal and thereof a substantially planar first clamping member having a first clamping surface, said hollow member being constructed of a radiolucent material;
  a sliding member comprising at a distal end thereof a substantially planar second clamping member having a second clamping surface, said first and second clamping members being cooperatively joined to said hollow and sliding members, respectively, so as to define a first clamping angle and a second clamping angle which allow the clamp to function in two different positions rotated from one another about the longitudinal axis of said hollow and sliding members, said sliding member being telescopically slidable within said hollow member to accommodate selective movement of said second clamping surface relative to said first clamping surface from a first clamping position to a second clamping position, said sliding member being also constructed of a radiolucent material;
  spring means cooperative with said hollow member and with said sliding member to maintain an essentially constant pressure when said clamp is in said first clamping position;
  finger wings attached to said hollow member at a distal end opposite the first clamping surface;
  a push knob attached to said sliding member at a distal end opposite the second clamping surface such that depressing said push knob relative to said hollow member telescopically extends said sliding member thereby permitting selective movement from one clamping position to another, such that said catheter may be gripped by said clamp when in said first clamping position so as to secure said catheter for insertion into said cystic duct, and such that thereafter said catheter may be released and said cystic duct clamped around said catheter when said clamp is in the second clamping position;
  orthogonal grooves located on said first clamping surface with matching orthogonal grooves located on said second clamping surface, said orthogonal grooves correspond with said first and second clamping angles thereby giving the clamp broad versatility of use; and
  means for preventing said sliding member from rotating within said hollow member.

32. A cholangiographic clamp as defined in claim 31, wherein one of said first or second clamping members comprises a radiopaque indicator means such that the clamp's location on the resultant x-ray may be identified without substantially obscuring the x-ray.

33. A cholangiographic clamp as defined in claim 31, wherein the first clamping angle is approximately 105° to 110° and the second clamping angle is approximately 90°.

34. A cholangiographic clamp as defined in claim 31, wherein said first clamping member contains visual indicator means which correspond with the orthogonal grooves on said first clamping surface.

35. A method wherein a surgical clamp comprising a hollow member with a substantially planar first clamping surface at the distal end thereof, a sliding member with a substantially planar second clamping surface at the distal end thereof being telescopically slidable within the hollow member, and means for releasably maintaining an essentially constant clamping pressure between the first and second clamping surfaces, a method of inserting a catheter into an anatomical duct and of thereafter clamping the duct around the catheter, the method comprising the steps of:
  telescopically sliding the sliding member in relation to the hollow member thereby grasping the catheter with the clamp at a first clamping position;
  inserting the catheter into the duct;
  telescopically sliding the sliding member in relation to the hollow member thereby releasing the catheter from the clamp; and
  clamping the duct around said catheter without occluding the catheter at a second clamping position.

36. A method as defined in claim 35, wherein the surgical clamp is intended for use in taking a cholangiogram, and wherein the anatomical duct is the cystic duct, and wherein the hollow member and the sliding member are constructed out a radiolucent material such that when the cholangiogram is taken the surgical clamp does not obscure the cholangiogram, the method further comprising the steps of:

injecting a diagnostic dye through the catheter; and taking a cholangiogram while the clamp is still in the second clamping position, securely clamping the cystic duct around the catheter.

37. A surgical clamp apparatus for inserting a catheter into an anatomical duct and for thereafter clamping the duct around the catheter, said apparatus comprising:

a first clamping surface and a second clamping surface which are moveable in relation to each other such that movement of said first clamping surface relative to said second clamping surface accomodates selective movement from a first clamping position to a second clamping position, said first and second clamping surfaces each comprising a groove formed thereon such that the grooves of said clamping surfaces cooperatively define an opening therebetween for receiving said catheter such that the clamp does not occlude said catheter when held in said opening; and means for releasably biasing said first clamping surface relative to said second clamping surface at a first clamping position, and for releasing said first clamping surface relative to said second clamping surface to accomodate movement of said first clamping surface to said second clamping position, said biasing means providing automatic closure upon release thereof so as to provide a predetermined, essentially constant clamping pressure between said first and second clamping surfaces which permits said clamping surfaces to self-adjust to securely clamp any one of various sizes of catheters and various sizes of anatomical ducts.

* * * * *

UNITED STATES PATENT AND TRADEMARK OFFICE
CERTIFICATE OF CORRECTION

PATENT NO. : 4,792,330

DATED : December 20, 1988

INVENTOR(S) : Harrison M. Lazarus et al.

It is certified that error appears in the above-identified patent and that said Letters Patent is hereby corrected as shown below:

Column 4, line 62, "FIG. 1 is perspective view" should be --FIG. 1 is a perspective view--

Column 6, line 5, "It will be appreciated other" should be --It will be appreciated that other--

Column 8, line 67, "member comprises" should be --members comprise--

Column 10, line 9, "member" should be --members--

Column 10, line 11, "clamps location" should be --clamp's location--

Column 11, line 19, "correspond" should be --corresponding--

Column 12, line 24, "correspond" should be --corresponding--

Column 12, line 67, "constructed out a" should be --constructed out of a--

Signed and Sealed this

Seventh Day of November, 1989

*Attest:*

JEFFREY M. SAMUELS

*Attesting Officer*   Acting Commissioner of Patents and Trademarks